United States Patent [19]
Saito et al.

[11] Patent Number: 5,580,956
[45] Date of Patent: Dec. 3, 1996

[54] PHOSPHOLIPASE C-INHIBITING PEPTIDES

[75] Inventors: Hiromitsu Saito, Mishima; Genkichi Ishikawa; Motoo Yamasaki, both of Machida; Yoshimi Honma, Shakujii-machi, all of Japan

[73] Assignee: Kyowa Hakko Kogyo Co., Ltd., Tokyo, Japan

[21] Appl. No.: 146,152
[22] PCT Filed: Mar. 11, 1993
[86] PCT No.: PCT/JP93/00299
 § 371 Date: Nov. 10, 1993
 § 102(e) Date: Nov. 10, 1993
[87] PCT Pub. No.: WO93/18062
 PCT Pub. Date: Sep. 16, 1993

Related U.S. Application Data

[63] Continuation-in-part of PCT/JP93/00299, published as WO93/18062, Mar. 11, 1993 Sep. 16, 1993.

[30] Foreign Application Priority Data

Mar. 11, 1992 [JP] Japan ..................... 4-052394

[51] Int. Cl.⁶ ................ A61K 38/00; C07K 7/00; C07K 5/00; C07K 17/00
[52] U.S. Cl. .............. 530/325; 530/326; 530/327; 530/328; 530/329
[58] Field of Search ........................ 530/325, 326, 530/327, 328, 329

[56] References Cited

PUBLICATIONS

Emori et al., *J. Biol. Chem.*, vol. 264, No. 36, pp. 21885–21890, Dec. 1989.
Ohta et al., *FEBS Lett*, vol. 242, No. 1, pp. 31–35, Dec. 1988.
Homma et al., *J. Biol. Chem.*, vol. 267, No. 30, pp. 21844–21849, Oct., 1992.
Homma, et al., Biochemical and Biophysical Research Communications, 182(3): 1402–1407 (1992).
S. G. Rhee, et al., Science 244, 546–550, 1989.
Y. Homma, et al., Biochemical Journal, 269, 13–18, 1990.
D. Anderson, et al., Science 250, 979–982, 1990.
Journal of Biological Chemistry, 261, 16838–16847, 1986.
Journal of Cell Biology, 105, 2745–2750, 1987.
Science, 232, 97–100, 1986.
Science, 248, 1009, 1990.
Biochemical and Biophysical Research Communications, 156, 846–854, 1988.
Biochemical Journal, 290, 649–653, 1993.
American Journal of Pathology, 139, 737–742, 1991.
The Journal of Antibiotics, vol. 45, No. 8, pp. 1365–1366.

*Primary Examiner*—Avis M. Davenport
*Attorney, Agent, or Firm*—Antonelli, Terry, Stout & Kraus

[57] ABSTRACT

The present invention relates to a peptide which has phospholipase C-inhibiting activity and which has the amino acid sequence defined in Sequence Listing by SEQ ID: No. 1; or a modified peptide in which one or more of the amino acid residues of the above mentioned peptide are deleted, or in which one or more amino acid residues are added to the above mentioned peptide, and/or in which one or more of the amino acid residues are substituted with other amino acid residues or modified amino acid residues.

3 Claims, No Drawings

SEQUENCE LISTING ( 1 ) GENERAL INFORMATION:

( i i i ) NUMBER OF SEQUENCES: 28

( 2 ) INFORMATION FOR SEQ ID NO: 1:

( i ) SEQUENCE CHARACTERISTICS:
        ( A ) LENGTH: 24 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 1:

```
Ser  Leu  Val  Glu  Leu  Val  Ser  Tyr  Tyr  Glu  Lys  His  Ala  Leu  Tyr  Arg
1                 5                           10                          15

Lys  Met  Arg  Leu  Arg  Tyr  Pro  Val
          20
```

( 2 ) INFORMATION FOR SEQ ID NO: 2:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 2:

```
Ser  Tyr  Tyr  Glu  Lys  His  Ala  Leu  Tyr  Arg  Lys  Met
```

```
1               5                   10
```

(2) INFORMATION FOR SEQ ID NO: 3:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO: 3:

```
Glu  Lys  His  Ala  Leu  Tyr  Arg  Lys  Met
1                   5
```

(2) INFORMATION FOR SEQ ID NO: 4:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO: 4:

```
Glu  Lys  His  Ala  Leu  Tyr  Arg  Lys  Met  Arg  Leu  Arg  Tyr  Pro  Val
1                   5                        10                       15
```

(2) INFORMATION FOR SEQ ID NO: 5:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO: 5:

```
Leu  Tyr  Arg  Lys  Met  Arg  Leu  Arg  Tyr  Pro  Val
1                   5                        10
```

(2) INFORMATION FOR SEQ ID NO: 6:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (xi) SEQUENCE DESCRIPTION: SEQ ID NO: 6:

```
Ser  Leu  Val  Glu  Leu  Val  Ser  Tyr  Tyr  Glu  Lys  His  Ala
1                   5                        10
```

(2) INFORMATION FOR SEQ ID NO: 7:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO: 7:

```
Tyr  Arg  Lys  Met  Arg  Leu  Arg  Tyr
1                   5
```

(2) INFORMATION FOR SEQ ID NO: 8:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 8:

Arg Lys Met Arg Leu Arg
1               5

( 2 ) INFORMATION FOR SEQ ID NO: 9:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 8
        ( C ) IDENTIFICATION METHOD:by experiment
        ( D ) OTHER INFORMATION:Xaa represents L-Tyrosine amide.

( x i ) SEQUENCE DESCRIPTION: SEQ ID NO: 9:

Tyr Arg Lys Met Arg Leu Arg Xaa
1               5

( 2 ) INFORMATION FOR SEQ ID NO: 10:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( C ) IDENTIFICATION METHOD:by experiment
        ( D ) OTHER INFORMATION:Xaa in Location 1 represents N-Acetyl-L-
              Tyrosine.
        ( A ) NAME/KEY: Modified-site
        ( B ) LOCATION: 8
        ( C ) IDENTIFICATION METHOD:by experiment
        ( D ) OTHER INFORMATION:Xaa in Location 8 represents L-Tyrosine
              amide.

( x i ) SEQUENCE DESCRIPTION: SEQ ID NO: 10:

Xaa Arg Lys Met Arg Leu Arg Xaa
1               5

( 2 ) INFORMATION FOR SEQ ID NO: 11:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( C ) IDENTIFICATION METHOD: by experiment
        ( D ) OTHER INFORMATION: Xaa in Location 1 represents
              N-(n- Butyryl)-L-Leucine.
        ( A ) NAME/KEY: Modified-site
        ( B ) LOCATION: 11
        ( C ) IDENTIFICATION METHOD: by experiment
        ( D ) OTHER INFORMATION: Xaa in Location 11 represents L-Valine amide.

( x i ) SEQUENCE DESCRIPTION: SEQ ID NO: 11:

Xaa Tyr Arg Lys Met Arg Leu Arg Tyr Pro Xaa
1               5                   10

( 2 ) INFORMATION FOR SEQ ID NO: 12:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( C ) IDENTIFICATION METHOD: by experiment
        ( D ) OTHER INFORMATION: Xaa in Location 1 represents
            N-Coumalyl-L- Leucine.
        ( A ) NAME/KEY: Modified-site
        ( B ) LOCATION: 11
        ( C ) IDENTIFICATION METHOD: by experiment
        ( D ) OTHER INFORMATION: Xaa in Location 11 represents L-Valine
            amide.

( x i ) SEQUENCE DESCRIPTION: SEQ ID NO: 12:

Xaa Tyr Arg Lys Met Arg Leu Arg Tyr Pro Xaa
1               5                   10

( 2 ) INFORMATION FOR SEQ ID NO: 13:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( C ) IDENTIFICATION METHOD: by experiment
        ( D ) OTHER INFORMATION: Xaa in Location 1 represents N-(2,3-
            Dihydroxybenzoyl)-L-Leucine.
        ( A ) NAME/KEY: Modified-site
        ( B ) LOCATION: 11
        ( C ) IDENTIFICATION METHOD: by experiment
        ( D ) OTHER INFORMATION: Xaa in Location 11 represents L-Valine
            amide.

( x i ) SEQUENCE DESCRIPTION: SEQ ID NO: 13:

Xaa Tyr Arg Lys Met Arg Leu Arg Tyr Pro Xaa
1               5                   10

( 2 ) INFORMATION FOR SEQ ID NO: 14:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( C ) IDENTIFICATION METHOD: by experiment
        ( D ) OTHER INFORMATION: Xaa in Location 1 represents N-(2,4-
            Dihydroxybenzoyl)-L-Leucine.
        ( A ) NAME/KEY: Modified-site
        ( B ) LOCATION: 11
        ( C ) IDENTIFICATION METHOD: by experiment (D) OTHER INFORMATION: Xaa in Location 11 represents L-Valine
amide.

(x i) SEQUENCE DESCRIPTION: SEQ ID NO: 14:

Xaa Tyr Arg Lys Met Arg Leu Arg Tyr Pro Xaa
1               5                   10

(2) INFORMATION FOR SEQ ID NO: 15:

(i) SEQUENCE CHARACTERISTICS:
    (A) LENGTH: 11 amino acids
    (B) TYPE: amino acid
    (D) TOPOLOGY: linear (i i) MOLECULE TYPE: peptide (i x) FEATURE:
    (A) NAME/KEY: Modified-site
    (B) LOCATION: 1
    (C) IDENTIFICATION METHOD: by experiment
    (D) OTHER INFORMATION: Xaa in Location 1 represents N-(2,5-
        Dihydroxybenzoyl)-L-Leucine.
    (A) NAME/KEY: Modified-site
    (B) LOCATION: 11
    (C) IDENTIFICATION METHOD: by experiment
    (D) OTHER INFORMATION: Xaa in Location 11 represents L-Valine
        amide.

(x i) SEQUENCE DESCRIPTION: SEQ ID NO: 15:

Xaa Tyr Arg Lys Met Arg Leu Arg Tyr Pro Xaa
1               5                   10

(2) INFORMATION FOR SEQ ID NO: 16:

(i) SEQUENCE CHARACTERISTICS:
    (A) LENGTH: 11 amino acids
    (B) TYPE: amino acid
    (D) TOPOLOGY: linear (i i) MOLECULE TYPE: peptide (i x) FEATURE:
    (A) NAME/KEY: Modified-site
    (B) LOCATION: 1
    (C) IDENTIFICATION METHOD: by experiment
    (D) OTHER INFORMATION: Xaa in Location 1 represents N-(3-
        Cyclohexylpropionyl)-L-Leucine.
    (A) NAME/KEY: Modified-site
    (B) LOCATION: 11
    (C) IDENTIFICATION METHOD: by experiment
    (D) OTHER INFORMATION: Xaa in Location 11 represents L-Valine
        amide.

(x i) SEQUENCE DESCRIPTION: SEQ ID NO: 16:

Xaa Tyr Arg Lys Met Arg Leu Arg Tyr Pro Xaa
1               5                   10

(2) INFORMATION FOR SEQ ID NO: 17:

(i) SEQUENCE CHARACTERISTICS:
    (A) LENGTH: 11 amino acids
    (B) TYPE: amino acid
    (D) TOPOLOGY: linear (i i) MOLECULE TYPE: peptide (i x) FEATURE:
    (A) NAME/KEY: Modified-site
    (B) LOCATION: 1
    (C) IDENTIFICATION METHOD: by experiment
    (D) OTHER INFORMATION: Xaa in Location 1 represents N-
        Cyclopentylacetyl-L-Leucine.
    (A) NAME/KEY: Modified-site
    (B) LOCATION: 11

(C) IDENTIFICATION METHOD: by experiment
(D) OTHER INFORMATION: Xaa in Location 11 represents L-Valine
amide.

(x i) SEQUENCE DESCRIPTION: SEQ ID NO: 17:

Xaa  Tyr  Arg  Lys  Met  Arg  Leu  Arg  Tyr  Pro  Xaa
1                  5                             10

(2) INFORMATION FOR SEQ ID NO: 18:

(i) SEQUENCE CHARACTERISTICS:
   (A) LENGTH: 11 amino acids
   (B) TYPE: amino acid
   (D) TOPOLOGY: linear (i i) MOLECULE TYPE: peptide (i x) FEATURE:
   (A) NAME/KEY: Modified-site
   (B) LOCATION: 1
   (C) IDENTIFICATION METHOD: by experiment
   (D) OTHER INFORMATION: Xaa in Location 1 represents
       N-Propionyl- L-Leucine.
   (A) NAME/KEY: Modified-site
   (B) LOCATION: 11
   (C) IDENTIFICATION METHOD: by experiment
   (D) OTHER INFORMATION: Xaa in Location 11 represents L-Valine
       amide.

(x i) SEQUENCE DESCRIPTION: SEQ ID NO: 18:

Xaa  Tyr  Arg  Lys  Met  Arg  Leu  Arg  Tyr  Pro  Xaa
1                  5                             10

(2) INFORMATION FOR SEQ ID NO: 19:

(i) SEQUENCE CHARACTERISTICS:
   (A) LENGTH: 11 amino acids
   (B) TYPE: amino acid
   (D) TOPOLOGY: linear (i i) MOLECULE TYPE: peptide (i x) FEATURE:
   (A) NAME/KEY: Modified-site
   (B) LOCATION: 1
   (C) IDENTIFICATION METHOD: by experiment
   (D) OTHER INFORMATION: Xaa in Location 1 represents
       N-Isobutyryl- L-Leucine.
   (A) NAME/KEY: Modified-site
   (B) LOCATION: 11
   (C) IDENTIFICATION METHOD: by experiment
   (D) OTHER INFORMATION: Xaa in Location 11 represents L-Valine
       amide.

(x i) SEQUENCE DESCRIPTION: SEQ ID NO: 19:

Xaa  Tyr  Arg  Lys  Met  Arg  Leu  Arg  Tyr  Pro  Xaa
1                  5                             10

(2) INFORMATION FOR SEQ ID NO: 20:

(i) SEQUENCE CHARACTERISTICS:
   (A) LENGTH: 11 amino acids
   (B) TYPE: amino acid
   (D) TOPOLOGY: linear (i i) MOLECULE TYPE: peptide (i x) FEATURE:
   (A) NAME/KEY: Modified-site
   (B) LOCATION: 1
   (C) IDENTIFICATION METHOD: by experiment
   (D) OTHER INFORMATION: Xaa in Location 1 represents
       N-(2-Ethyl-n- butyryl)-L-Leucine.
   (A) NAME/KEY: Modified-site (B) LOCATION: 11
(C) IDENTIFICATION METHOD: by experiment
(D) OTHER INFORMATION: Xaa in Location 11 represents L-Valine
amide.

(x i) SEQUENCE DESCRIPTION: SEQ ID NO: 20:

```
Xaa  Tyr  Arg  Lys  Met  Arg  Leu  Arg  Tyr  Pro  Xaa
1                  5                            10
```

(2) INFORMATION FOR SEQ ID NO: 21:

(i) SEQUENCE CHARACTERISTICS:
(A) LENGTH: 11 amino acids
(B) TYPE: amino acid
(D) TOPOLOGY: linear (i i) MOLECULE TYPE: peptide (i x) FEATURE:
(A) NAME/KEY: Modified-site
(B) LOCATION: 1
(C) IDENTIFICATION METHOD: by experiment
(D) OTHER INFORMATION: Xaa in Location 1 represents
N-(n- Caprylyl)-L-Leucine.
(A) NAME/KEY: Modified-site
(B) LOCATION: 11
(C) IDENTIFICATION METHOD: by experiment
(D) OTHER INFORMATION: Xaa in Location 11 represents L-Valine
amide.

(x i) SEQUENCE DESCRIPTION: SEQ ID NO: 21:

```
Xaa  Tyr  Arg  Lys  Met  Arg  Leu  Arg  Tyr  Pro  Xaa
1                  5                            10
```

(2) INFORMATION FOR SEQ ID NO: 22:

(i) SEQUENCE CHARACTERISTICS:
(A) LENGTH: 11 amino acids
(B) TYPE: amino acid
(D) TOPOLOGY: linear (i i) MOLECULE TYPE: peptide (i x) FEATURE:
(A) NAME/KEY: Modified-site
(B) LOCATION: 1
(C) IDENTIFICATION METHOD: by experiment
(D) OTHER INFORMATION: Xaa in Location 1 represents
N-Succinyl-L- Leucine.
(A) NAME/KEY: Modified-site
(B) LOCATION: 11
(C) IDENTIFICATION METHOD: by experiment
(D) OTHER INFORMATION: Xaa in Location 11 represents L-Valine
amide.

(x i) SEQUENCE DESCRIPTION: SEQ ID NO: 22:

```
Xaa  Tyr  Arg  Lys  Met  Arg  Leu  Arg  Tyr  Pro  Xaa
1                  5                            10
```

(2) INFORMATION FOR SEQ ID NO: 23:

(i) SEQUENCE CHARACTERISTICS:
(A) LENGTH: 11 amino acids
(B) TYPE: amino acid
(D) TOPOLOGY: linear (i i) MOLECULE TYPE: peptide (i x) FEATURE:
(A) NAME/KEY: Modified-site
(B) LOCATION: 1
(C) IDENTIFICATION METHOD: by experiment
(D) OTHER INFORMATION: Xaa in Location 1 represents N-(3-
Cyclopentylpropionyl)-L-Leucine.

( A ) NAME/KEY: Modified-site
                    ( B ) LOCATION: 11
                    ( C ) IDENTIFICATION METHOD: by experiment
                    ( D ) OTHER INFORMATION: Xaa in Location 11 represents L-Valine
                        amide.

( x i ) SEQUENCE DESCRIPTION: SEQ ID NO: 23:

Xaa Tyr Arg Lys Met Arg Leu Arg Tyr Pro Xaa
1               5                   10

( 2 ) INFORMATION FOR SEQ ID NO: 24:

( i ) SEQUENCE CHARACTERISTICS:
                    ( A ) LENGTH: 11 amino acids
                    ( B ) TYPE: amino acid
                    ( D ) TOPOLOGY: linear ( i i ) MOLECULE TYPE: peptide ( i x ) FEATURE:
                    ( A ) NAME/KEY: Modified-site
                    ( B ) LOCATION: 1
                    ( C ) IDENTIFICATION METHOD: by experiment
                    ( D ) OTHER INFORMATION: Xaa in Location 1 represents N-
                        Cyclopropylcarbonyl-L-Leucine.
                    ( A ) NAME/KEY: Modified-site
                    ( B ) LOCATION: 11
                    ( C ) IDENTIFICATION METHOD: by experiment
                    ( D ) OTHER INFORMATION: Xaa in Location 11 represents L-Valine
                        amide.

( x i ) SEQUENCE DESCRIPTION: SEQ ID NO: 24:

Xaa Tyr Arg Lys Met Arg Leu Arg Tyr Pro Xaa
1               5                   10

( 2 ) INFORMATION FOR SEQ ID NO: 25:

( i ) SEQUENCE CHARACTERISTICS:
                    ( A ) LENGTH: 11 amino acids
                    ( B ) TYPE: amino acid
                    ( D ) TOPOLOGY: linear ( i i ) MOLECULE TYPE: peptide ( i x ) FEATURE:
                    ( A ) NAME/KEY: Modified-site
                    ( B ) LOCATION: 1
                    ( C ) IDENTIFICATION METHOD: by experiment
                    ( D ) OTHER INFORMATION: Xaa in Location 1 represents N-
                        Cyclohexylacetyl-L-Leucine.
                    ( A ) NAME/KEY: Modified-site
                    ( B ) LOCATION: 11
                    ( C ) IDENTIFICATION METHOD: by experiment
                    ( D ) OTHER INFORMATION: Xaa in Location 11 represents L-Varine
                        amide.

( x i ) SEQUENCE DESCRIPTION: SEQ ID NO: 25:

Xaa Tyr Arg Lys Met Arg Leu Arg Tyr Pro Xaa
1               5                   10

( 2 ) INFORMATION FOR SEQ ID NO: 26:

( i ) SEQUENCE CHARACTERISTICS:
                    ( A ) LENGTH: 11 amino acids
                    ( B ) TYPE: amino acid
                    ( D ) TOPOLOGY: linear ( i i ) MOLECULE TYPE: peptide ( i x ) FEATURE:
                    ( A ) NAME/KEY: Modified-site
                    ( B ) LOCATION: 1
                    ( C ) IDENTIFICATION METHOD: by experiment
                    ( D ) OTHER INFORMATION: Xaa in Location 1 represents N-Cyclopentylcarbonyl-L-Leucine.
(A) NAME/KEY: Modified-site
(B) LOCATION: 11
(C) IDENTIFICATION METHOD: by experiment
(D) OTHER INFORMATION: Xaa in Location 11 represents L-Valine amide.

(xi) SEQUENCE DESCRIPTION: SEQ ID NO: 26:

```
Xaa  Tyr  Arg  Lys  Met  Arg  Leu  Arg  Tyr  Pro  Xaa
1                  5                        10
```

(2) INFORMATION FOR SEQ ID NO: 27:

(i) SEQUENCE CHARACTERISTICS:
(A) LENGTH: 11 amino acids
(B) TYPE: amino acid
(D) TOPOLOGY: linear (ii) MOLECULE TYPE: peptide (ix) FEATURE:
(A) NAME/KEY: Modified-site
(B) LOCATION: 1
(C) IDENTIFICATION METHOD: by experiment
(D) OTHER INFORMATION: Xaa in Location 1 represents N-(n-Hexanoyl)-L-Leucine.
(A) NAME/KEY: Modified-site
(B) LOCATION: 11
(C) IDENTIFICATION METHOD: by experiment
(D) OTHER INFORMATION: Xaa in Location 11 represents L-Valine amide.

(xi) SEQUENCE DESCRIPTION: SEQ ID NO: 27:

```
Xaa  Tyr  Arg  Lys  Met  Arg  Leu  Arg  Tyr  Pro  Xaa
1                  5                        10
```

(2) INFORMATION FOR SEQ ID NO: 28:

(i) SEQUENCE CHARACTERISTICS:
(A) LENGTH: 11 amino acids
(B) TYPE: amino acid
(D) TOPOLOGY: linear (ii) MOLECULE TYPE: peptide (ix) FEATURE:
(A) NAME/KEY: Modified-site
(B) LOCATION: 1
(C) IDENTIFICATION METHOD: by experiment
(D) OTHER INFORMATION: Xaa in Location 1 represents N-(n-Nonanoyl)-L-Leucine.
(A) NAME/KEY: Modified-site
(B) LOCATION: 11
(C) IDENTIFICATION METHOD: by experiment
(D) OTHER INFORMATION: Xaa in Location 11 represents L-Valine amide.

(xi) SEQUENCE DESCRIPTION: SEQ ID NO: 28:

```
Xaa  Tyr  Arg  Lys  Met  Arg  Leu  Arg  Tyr  Pro  Xaa
1                  5                        10
```

PHOSPHOLIPASE C-INHIBITING PEPTIDES

This application is a 371 continuation-in-part of PCT/JP93/00299 filed Mar. 11, 1993 and published as WO93/18062 Sep. 16, 1993.

TECHNICAL FIELD

The present invention relates to novel peptides which have phospholipase C (hereinafter referred to as PLC)-inhibiting activity.

PRIOR ART

The isolation and purification, from various tissues, of PLC, for example, phospholipid inositol PLC (hereinafter referred to as PI-PLC), has been carried out in order to understand the mechanism of intracellular signal transduction pathway, and heretofore, the existence of 9 different isozymes thereof classified into 4 types, α, β, γ and δ has been found. Two types are known as γ type, $\gamma_1$ and $\gamma_2$ (S. G. Rhee et al., Science, 244, 546–550, 1989; Y. Homma et al., Biochemical Journal, 269, 13–18, 1990), and both have been shown to play an important role in the signal transduction of growth factor. The structural characteristics of β, γ and δ types is that oncogene src Homology regions, SH2 and SH3 (SH2/SH3) regions are located between I and II regions commonly found in β, γ and δ, and the SH2 region of the γ type is essential for interaction with receptor-type tyrosine kinase (D. Anderson et al., Science, 250, 979–982, 1990). The function of the SH3 region of the γ type is not clear, but it has been suggested that it is important for interaction with the cytoskeletal system. Also, with the discovery of the oncogene crk which has SH2 and SH3 (SH2/SH3) regions but no kinase region, attention has centered on the possibility that disturbances in the regulation via the SH2 and SH3 (SH2/SH3) regions of the γ type (abnormalities in PI-PLC activation) and cell proliferation abnormalities may lead to canceration. Furthermore, there has been reports showing that elevated PLC activity is related with pathology, among them a report that PLC contributes to the thrombin-induced platelet activation system (Journal of Biological Chemistry, 261, 16838–16847, 1986), a report that PLC activity contributes to the release of histamine (Journal of Cell Biology, 105, 2745–2750, 1987), a report that PLC contributes to the signal transduction pathway of the receptor for N-formyl-methionyl-leucyl-phenylalanine, which is known as a substance which provokes inflammation by means of granulocytes and polymorphonuclear leukocytes (PMNs) (Science, 232, 97–100, 1986), a report that the platelet-derived growth factor (PDGF) β-chain protein is expressed in large amounts in arteriosclerotic lesions (Science, 248, 1009, 1990), a report that PLC-$\gamma_2$ is present as a constituent of the signal transduction for PDGF-dependent proliferation of vascular smooth muscle cells, and is prominently involved in the proliferation of smooth muscle cells (Biochemical and Biophysical Research Communications, 156, 846–854, 1988; Biochemical Journal, 290, 649–653, 1993) and a report that PLC is stimulated in conditions of Alzheimer's disease (American Journal of Pathology, 139, 737–742, 1991). It is expected that the pathological conditions may be improved by inhibiting PLC activity, and thus it has been sought to provide an inhibiting agent against PLC activity. As peptides which have PLC inhibiting activity, the peptides defined in Sequence Listing by SEQ ID: Nos. 1–5, 7 and 8 have been published in the Journal of Biological Chemistry, Vol. 267, pp. 21844–21849, 1992, subsequent to the application (Japanese Unexamined Unpublished Patent No. 52394/92; Date of application: Mar. 11, 1992) on which the convention priority of the present application is founded.

DISCLOSURE OF THE INVENTION

According to the present invention, provided is a peptide which has phospholipase C-inhibiting activity and has the amino acid sequence as defined in Sequence Listing by SEQ ID: No. 1; or a modified peptide in which one or more of the amino acid residues of the above-mentioned peptide are deleted, in which one or more amino acid residues are added to the above mentioned peptide, and/or in which one or more of the amino acid residues are substituted with other amino acid residues or modified amino acid residues. The peptides are collectively named Compound (I). Examples of modified peptides include a peptide consisting of any one of the amino acid sequences defined in Sequence Listing by SEQ ID: Nos. 2–8, and a peptide represented by the formula W-X-Tyr-Arg-Lys-Met-Arg-Leu-Arg-Tyr-Y-Z (wherein W represents a hydrogen atom, a substituted or unsubstituted alkanoyl group, a substituted or unsubstituted aroyl group or a coumalyl group; X represents a single bond or -Leu-; Y represents a single bond or -Pro-Val-; and Z represents a hydroxy group or amino group, provided that Z represents an amino group when W represents a hydrogen atom), for example, a peptide consisting of any one of the amino acid sequences defined in Sequence Listing by SEQ ID: Nos. 9–28. The peptides consisting of the amino acid sequences defined in Sequence Listing by SEQ ID: Nos. 1–28 are named Compounds (I-1)–(I-28), respectively.

In the above formulae, the substituted or unsubstituted alkanoyl group has 1–10 carbon atoms, and examples of which include formyl, acetyl, propionyl, butyryl, isobutyryl, valeryl, isovaleryl and pivaloyl groups. Examples of the substituent include a carboxy group, an alicyclic alkyl group and a phenyl group. Examples of the alicyclic alkyl group include a cyclopropyl, cyclobutyl, cyclopentyl and cyclohexyl group of 3–8 carbon atoms. Examples of the substituted or unsubstituted aroyl group may be a benzoyl group and naphthoyl group. The substituent may be 1–3 hydroxy groups.

Compound (I) is synthesized according to a solid phase synthetic method using an automated peptide synthesizer. A solid phase carrier to which a peptide is bound as obtained by the solid phase method is treated with hydrogen fluoride, whereby the peptide is freed from the solid phase carrier and at the same time the protective groups on the amino acid side chains are removed. For the amidization of the C-terminal amino acid, when an Applied Biosystems (Applied Biosystems, Inc., Foster City, Calif., U.S.A.; hereinafter referred to as "ABI") peptide synthesizer is employed, a p-methyl-benzhydrylamine (BHA)-resin (product of ABI Co.) is used; and when a Shimazu Seisakusho peptide synthesizer is employed, a Rink amide-resin or Rink amide-MBHA (4-methyl-benzhydrylamine)-resin (product of Carbiochem-Novabiochem Japan, Inc.) is used. Furthermore, for the modification (acylation) of the N-terminal amino acid, the N-terminal amino acid protected group is condensed, after removal of the protecting group, using a carboxylic acid component and a condensing reagent [for example, benzotriazole-1-yl-oxy-tris-pyrrolidino-phosphonium hexafluorophosphate L(PyBOP)/N-hydroxybenzotriazole (HOBT)/N-methylmorpholine (NMM)] as in the extension of the peptide chain. Alternatively, the condensation is carried out using an activated carboxylic acid compound such as an acid anhydride and an acid chloride of a carboxylic acid component. The above-mentioned reaction is carried out on a synthetic resin, and after the completion of the reaction, the desired peptide derivative is obtained by cleavage from the resin. The crude product thus obtained is purified by high performance liquid chromatography (hereinafter referred to as HPLC) using a reverse phase column to obtain a pure peptide.

Compound (I) obtained by the present invention exhibits an excellent PLC-inhibiting activity, cell proliferation-inhibiting activity and antibacterial activity.

The PLC-inhibiting activity, cell proliferation-inhibiting activity and antibacterial activity of Compound (I) are demonstrated by the following test examples 1–3.

Experiment 1: PLC-inhibiting activity

A sample (PLC-$\gamma_1$) was prepared from bovine thymus according to the method of Y. Homma et al. described in Biochemical Journal [(Biochem. J.), 269, 13 (1990)].

A solution having the composition listed in Table 1 below was prepared in advance on the ice and the reaction was begun with heating to 37° C. After incubation for 10 minutes, 2 ml of a solution mixture of chloroform/methanol (2:1, V/V) was added thereto to stop the reaction. The resulting inositol phosphate was extracted with 0.5 ml of 1N hydrochloric acid. Two-phase distribution was carried out by centrifugation (2000×g, 3 minutes), and the amount of $^3$H contained in 0.7 ml of the supernatant was measured with scintillation counter.

TABLE 1

| Solution | Volume (µl) |
| --- | --- |
| Sample (0.2 µg purified PI-PLC-$\gamma_1$ sample) | 10 |
| Reaction solution | 30 |
| 1) 1M MES[a] NaOH buffer solution (pH 6.0) | 2.5 |
| 2) 1 mM CaCl$_2$ | 5 |
| 3) 20 mg/ml bovine serum albumin | 2.5 |
| 4) Aqueous solution of test peptide[b] | 20 |
| Substrate[c] | 10 |

[a]2-(N-morpholino)ethanesulfonic acid
[b]The peptides provided for the test and the concentrations of the aqueous solutions are shown in Table 2.
[c]500 µg phosphatidylinositol 4,5-bisphosphate (PIP$_2$), 150 µg phosphatidylethanolamine and 37 kBq [$^3$H]PIP$_2$ are mixed with a small amount of chloroform in advance. The lipid is dried to hardness under a nitrogen atmosphere, and 1 ml of 0.1M KCl is added thereto prior to ultrasonic treatment.

The obtained value of specific radioactivity was defined as "A", the value of specific radioactivity obtained when an equivalent amount of water was added instead of the aqueous solution of the test peptide was defined as "B", the value of specific radioactivity obtained when an equivalent amount of water was added instead of the sample and the aqueous solution of the test peptide was defined as "C", and the inhibition rate (X) was determined according to the following equation.

$$X(\%) = (A-C)/(B-C) \times 100$$

The inhibition rates of the test peptides are shown in Table 2.

TABLE 2

| Compound | Concentration (µM) | Inhibition rate (%) |
| --- | --- | --- |
| (I-1) | 15 | 55 |
| (I-1) | 55 | 88 |
| (I-4) | 120 | 73 |
| (I-5) | 125 | 70 |

TABLE 2-continued

| Compound | Concentration (µM) | Inhibition rate (%) |
| --- | --- | --- |
| (I-6) | 105 | 70 |
| (I-7) | 120 | 70 |
| (I-9) | 850 | 34 |
| (I-10) | 160 | 26 |
| (I-11) | 130 | 31 |
| (I-12) | 120 | 40 |
| (I-13) | 610 | 89 |
| (I-14) | 120 | 45 |
| (I-15) | 120 | 41 |
| (I-16) | 120 | 51 |
| (I-17) | 120 | 53 |
| (I-18) | 650 | 66 |
| (I-19) | 640 | 67 |
| (I-20) | 630 | 74 |
| (I-21) | 120 | 86 |
| (I-22) | 130 | 36 |
| (I-23) | 120 | 53 |
| (I-24) | 120 | 55 |
| (I-25) | 120 | 50 |
| (I-26) | 130 | 23 |
| (I-27) | 130 | 35 |
| (I-28) | 120 | 78 |

Experiment 2: Cell proliferation-inhibiting activity

The following procedure was carried out with an Amersham Cell Proliferation Detection Kit.

First, cells [KMS-4; M. Nanba et al., International Journal of Cancer, 32, 697 (1983)] were suspended in a DMEM culture medium (product of Nissui Seiyaku) containing 10% fetal calf serum to a concentration of 1–2×10$^4$ cells/ml, and 1 ml of the above-mentioned cell suspension was put into each well of a 24-well plate (product of Corning Co.). The cells were cultured for 2 days in a CO$_2$ incubator (37° C., 5% CO$_2$). Next, the culture medium was exchanged with a DMEM medium containing 10% fetal calf serum, and then the test peptide was added thereto and culturing was carried out for 17 hours. The culture medium was again exchanged with a serum-free DMEM medium, 0.5 ml of a solution of the reagents labelled 5-bromo-2'-deoxyuridine (BrdU) and 5-fluoro-2'-deoxyuridine (FdU) [10:1] diluted 1000-fold with the same medium was added to each well, and cultured for 2 hours. The culture medium was removed, and the cells were immobilized with an acetic acid/ethanol solution. The immobilized cells were stained according to the method for the Amersham Cell Proliferation Kit, and then further stained with a 1% Giemsa solution (product of Merck Co.). The number of cells incorporating BrdU and the total cell count within 1 field of vision of the microscope (approximately 200 cells) were determined, and the proportion (%) of stained cells per field of vision was calculated. Furthermore, the same procedure was repeated 10 times, and the average value thereof was defined as the cell proliferation activity (%).

The cell proliferation-inhibiting activity was calculated in the following manner. The proliferation activity without addition of peptide was defined as "A", the proliferation activity with addition of the test peptide was defined as "B", and the cell proliferation inhibition rate (X) was determined according to the following equation.

$$X(\%) = (1 - B/A) \times 100$$

The inhibition rates of the test peptides are shown in Table 3.

TABLE 3

| Compound | Concentration (μM) | Inhibition rate (%) |
|---|---|---|
| (I-7) | 42 | 5 |
| (I-9) | 42 | 50 |
| (I-10) | 42 | 50 |
| (I-11) | 32 | 84 |
| (I-11) | 1 | 86 |
| (I-12) | 31 | 69 |
| (I-13) | 31 | 69 |
| (I-14) | 31 | 59 |
| (I-15) | 31 | 66 |
| (I-16) | 31 | 84 |
| (I-17) | 31 | 72 |
| (I-18) | 32 | 44 |
| (I-19) | 32 | 59 |
| (I-20) | 31 | 44 |
| (I-21) | 31 | 56 |
| (I-22) | 31 | 84 |
| (I-23) | 31 | 53 |
| (I-24) | 32 | 66 |
| (I-25) | 31 | 75 |
| (I-26) | 31 | 71 |
| (I-27) | 31 | 28 |
| (I-28) | 31 | 22 |

Experiment 3: Antibacterial activity

The minimum growth inhibition concentrations (MIC) against various bacteria are shown in Tables 4-1 and 4-2. The antibacterial activity was determined by the agar dilution method using a culture medium (pH 7.0) containing 3 g/l bactotrypton (product of Difco Co.), 1 g/l meat extract, 1 g/l glucose and 16 g/l agar. The results are shown in Tables 4-1 and 4-2.

TABLE 4-1

| | MIC (μg/ml) | | |
|---|---|---|---|
| Test strain | (I-10) | (I-19) | (I-20) |
| Proteus vulgaris ATCC6897 | 83 | 83 | 83 |
| Shigella sonnei ATCC9290 | — | — | — |
| Salmonella typhi ATCC9902 | — | — | — |
| Pseudomonas aeruginosa Bin H No. 1 | 83 | 83 | 83 |
| Enterococcus faecium ATCC10541 | 83 | — | — |
| Bacillus subtilis No. 10107 | 83 | — | — |

—: No activity

TABLE 4-2

| | MIC (μg/ml) | | |
|---|---|---|---|
| Test strain | (I-22) | (I-26) | (I-27) |
| Proteus vulgaris ATCC6897 | 83 | 83 | 83 |
| Shigella sonnei ATCC9290 | — | — | 83 |
| Salmonella typhi ATCC9902 | — | — | 83 |
| Pseudomonas aeruginosa Bin H No. 1 | 42 | 42 | 42 |
| Enterococcus faecium ATCC10541 | — | — | 83 |
| Bacillus subtilis No. 10107 | — | — | 83 |

—: No activity

BEST MODE FOR CARRYING OUT THE INVENTION

The physiological properties reported in the following examples were determined using the instruments listed below.

Mass analysis: Examples 1–11, Hitachi M-80B

Examples 12–28, Nihon Denshi JMS-HX110A

Amino acid analysis: Waters pico tag

The abbreviations for the amino acids and their protective groups are used according to the recommendation [Biochemistry, 11, 1726 (1972)] of IUPAC-IUB Commission on Biochemical Nomenclature relating to biochemical nomenclature.

The following abbreviations represent the corresponding amino acids and protecting groups listed below.

Gly: Glycine
Ala: L-Alanine
Val: L-valine
Leu: L-leucine
Ile: L-isoleucine
Ser: L-serine
Thr: L-threonine
Asp: L-aspartic acid
Asn: L-asparagine
Glu: L-glutamic acid
Gln: L-glutamine
Lys: L-lysine
Met: L-methionine
His: L-histidine
Arg: L-arginine
Phe: L-phenylalanine
Tyr: L-tyrosine
Cys: L-cysteine
Pro: L-proline
Asx: L-aspartic acid or L-asparagine
Glx: L-glutamic acid or L-glutamine
t-Boc: t-butyloxycarbonyl
Bzl: benzyl
Tos: p-toluenesulfonyl
DNP: 2,4-dinitrophenyl
BOM: benzyloxymethyl
Cl-Z: 2-chlorobenzyloxycarbonyl
Br-Z: 2-bromobenzyloxycarbonyl
Fmoc: 9-fluorenylmethyloxycarbonyl The following abbreviations represent the corresponding side chain protected amino acids listed below.

Fmoc-Tyr(t-Bu)-OH:
  Nα-9-fluorenylmethyloxycarbonyl-O-t-butyl-L-tyrosine
Fmoc-Lys(t-Boc)-OH:
  Nα-9-fluorenylmethyloxycarbonyl-N-ε-t-butyloxycarbonyl-L-lysine
Fmoc-Arg(Pmc)-OH:
  Nα-9-fluorenylmethyloxycarbonyl-N-δ-2,2,5,7,8-pentamethylchroman-6-sulfonyl-L-arginine The following abbreviations represent the corresponding reactive solvents and reactive reagents listed below.

PyBOP: benzotriazole-1-yl-oxy-tris-pyrrolidino-phosphonium hexafluorophosphate
HOBt: N-hydroxybenzotriazole
NMM: N-methylmorpholine
DMF: N,N-dimethylformamide
TFA: trifluoroacetic acid The following companies produced the carboxylic acids used for modification of the N-terminus.

Acetic anhydride: Kokusan Kagaku
n-butyric anhydride: Nacalaitesque
Isobutyric acid: Daiichi Kagaku Pharmaceutical
n-caproic acid: Wako Junyaku
Succinic anhydride: Aldrich
3-cyclopentylpropionic acid: Aldrich Coumalic acid
2,3-dihydroxybenzoic acid
2,4-dihydroxybenzoic acid 2,5-dihydroxybenzoic acid
3-cyclohexanepropionic acid
Cyclopentylacetic acid
Propionic acid Tokyo Kasei
2-ethyl-n-butyric acid
n-caprylic acid
Cyclopropanecarboxylic acid
Cyclohexylacetic acid
Cyclopentanecarboxylic acid
Pelargonic acid In the following Examples 1–11, each peptide was synthesized by operating a 430A peptide synthesizer, manufactured by ABI Co., and using reagents and solvents of ABI Co., according to the synthesis program of ABI Co. The condensation reactions of the amino acids were carried out under standard conditions, wherein asparagine, glutamine and arginine were coupled in the form of an active ester with 1-hydroxybenzotriazole, and the other amino acids were coupled in the form of symmetrical acid anhydrides.

In the following Examples 12–28, each peptide was synthesized by operating a PSSM8 peptide synthesizer, manufactured by Shimadzu Seisakusho and using reagents and solvents of Shimadzu Seisakusho, according to the synthesis program of Shimadzu Seisakusho. The condensation reactions of the amino acids were carried out under standard conditions following the Fmoc method ("Fundamentals and Experiments in Peptide Synthesis", Izumiya, Nobuo et al., Maruzen).

In addition, amino acid protecting groups and reagents produced by Kokusan Kagaku, Peptide Institute, Inc. or Carbiochem-Novabiochem Japan were used, if necessary.

EXAMPLE 1

Synthesis of Compound (I-2: Sequence No. 2)

H-Ser-Tyr-Tyr-Glu-Lys-His-Ala-Leu-
Tyr-Arg-Lys-Met-OH

A carrier resin(0.73 g) combined with 0.5 mmol of t-Boc-Met was put in the reactor of an automatic synthesizer, and the following treatment and washing procedure were carried out following the synthesis program of ABI Co.
(1) Treatment with methylene chloride solution containing 33% TFA (80 seconds)
(2) Treatment with methylene chloride solution containing 50% TFA (18.5 minutes)
(3) Washing with methylene chloride (3 times)
(4) Treatment with methylene chloride solution containing 10% diisopropylethylamine (1 minute×2 times)
(5) Washing with DMF (5 times)
(6) To the Met-bonded carrier resin obtained in steps (1)–(5) was added 4 ml of a DMF solution containing 1.0 mmol of a symmetric acid anhydride of t-Boc-Lys (Cl-Z), followed by stirring in the reactor for 18 minutes.
(7) Washing with methylene chloride (5 times )

In this manner, t-Boc-Lys(Cl-Z)-Met was synthesized on the carrier resin.

Next, t-Boc-Lys(Cl-Z)-Met-bound carrier resin thus obtained was subjected to the above-mentioned deprotecting steps (1)–(5), an active ester (HOBt) of t-Boc-Arg(Tos) was added thereto for a condensation reaction in step (6), and t-Boc-Arg(Tos)-Lys (Cl-Z)-Met was synthesized on the carrier resin after the washing in step (7). Steps (1)–(7) were repeated to obtain 1.92 g of a protected peptide-bound carrier resin.

In step (6), t-Boc-Tyr(Br-Z)-OH, t-Boc-Leu-OH, t-Boc-Ala-OH, t-Boc-His (DNP) -OH, t-Boc-Lys (Cl-Z)-OH, t-Boc-Glu (OBzl)-OH, t-Boc-Tyr (Br-Z)-OH, t-Boc-Tyr (Br-Z)-OH, t-Boc-Ser(Bzl)-OH were used in order. After the completion of the synthesis reaction, 4.8 ml DMF and 0.51 ml thiophenol were added to 0.96 g of the obtained carrier resin, and the mixture was stirred at room temperature for 1 hour. Then, the carrier resin obtained by filtration was washed with 20 ml DMF, 20 ml water, 20 ml ethanol and 20 ml methylene chloride, after which 0.90 g of the carrier resin was put in the reactor of an automatic synthesizer, and the above-mentioned deprotecting steps (1)–(5) were carried out according to the de-Boc program. To 0.87 g of the obtained carrier was added 1.1 ml anisol, and the mixture was allowed to stand for 15 hours, after which 15 ml hydrogen fluoride was added thereto and the mixture was stirred with cooling on ice for 1.2 hours. Next, the hydrogen fluoride was removed off under reduced pressure, 100 ml ethyl acetate was added to the carrier resin, and the mixture was stirred for half an hour. To the carrier resin obtained by filtration was added 100 ml of 2M acetic acid and the mixture was stirred for one hour. The carrier was removed by filtration, and the filtrate was freeze-dried to obtain 306 mg of a crude product. Then, 150 mg of the crude product was purified by HPLC using a reverse phase column (CAPCELL PACK C18 SG120 30×250 mm). The elution was carried out with a linear concentration gradient pattern using acetonitrile containing 0.1% TFA and with detection at 220 nm, fractions containing compound (I-2) were obtained. The fractions were freeze-dried to obtain 82.5 mg of Compound (I-2).

MS analysis (SIMS; the same shall be applied hereinafter): 1588 $(M+1)^+$

Amino acid analysis: Glx 1.0 (1), Ser 1.0 (1), His 1.1(1), Arg 1.2(1), Ala 1.0(1), Tyr 3.0(3), Met 0.8(1), Leu 1.0 (1), Lys 2.0 (2).

EXAMPLE 2

Synthesis of Compound (I-3: Sequence No. 3)

H-Glu-Lys-His-Ala-Leu-Tyr-Arg-Lys-Met-OH

In the same manner as in Example 1, 1.3 g of a protected peptide-bound carrier resin was obtained using t-Boc-Met-bound carrier resin and protected amino acids, t-Boc-Lys (Cl-Z)-OH, t-Boc-Arg (Tos)-OH, t-Boc-Tyr (Br-Z)-OH, t-Boc-Leu-OH, t-Boc-Ala-OH, t-Boc-His(DNP)-OH, t-Boc-Lys(Cl-Z)-OH and t-Boc-Glu(OBzl)-OH, in order. Next, 0.67 g of the carrier resin thus obtained was treated in the same manner as in Example 1 to obtain 140 mg of a crude product. Then, 67 mg of the crude product was purified by HPLC to obtain 24 mg of Compound (I-3).

MS analysis: 1175 $(M+1)^+$

Amino acid analysis: Glx 1.0(1), His 1.0(1), Arg 1.1(1), Ala 1.0(1), Tyr 1.0(1), Met 0.9(1), Leu 1.0(1), Lys 2.1 (2).

EXAMPLE 3

Synthesis of Compound (I-4: Sequence No. 4)

H-Glu-Lys-His-Ala-Leu-Tyr-Arg-Lys-Met
-Arg-Leu-Arg-Tyr-Pro-Val-OH

In the same manner as in Example 1, 2.5 g of a protected peptide-bound carrier resin was obtained using t-Boc-Val-bound carrier resin and protected amino acids, t-Boc-Pro-OH, t-Boc-Tyr (Br-Z)-OH, t-Boc-Arg (Tos)-OH, t-Boc-Leu-OH, t-Boc-Arg(Tos)-OH, t-Boc-Met-OH, t-Boc-Lys (Cl-Z)-

OH, t-Boc-Arg (Tos)-OH, t-Boc-Tyr (Br-Z)-OH, t-Boc-Leu-OH, t-Boc-Ala-OH, t-Boc-His (DNP)-OH, t-Boc-Lys (Cl-Z)-OH and t-Boc-Glu (OBzl)-OH, in order. Next, 1.24 g of the carrier resin thus obtained was treated in the same manner as in Example 1 to obtain 322 mg of a crude product. Then, 161 mg of the crude product was purified by HPLC to obtain 96 mg of Compound (I-4).

MS analysis: 1959 (M+1)$^+$

Amino acid analysis: Glx 0.9 (1), His 1.1 (1), Arg 3.1(3), Ala 0.9(1), Pro 1.4(1), Tyr 2.0(2), Val 0.8(1), Met 0.9(1), Leu 2.0(2), Lys 1.9(2).

EXAMPLE 4

Synthesis of Compound (I-5: Sequence No. 5)

H-Leu-Tyr-Arg-Lys-Met-Arg-Leu-Arg-Tyr-Pro-Val-OH

In the same manner as in Example 1, 1.6 g of a protected peptide-bound carrier resin was obtained using t-Boc-Val-bound carrier resin and protected amino acids, t-Boc-Pro-OH, t-Boc-Tyr (Br-Z)-OH, t-Boc-Arg (Tos)-OH, t-Boc-Leu-OH, t-Boc-Arg(Tos)-OH, t-Boc-Met-OH, t-Boc-Lys (Cl-Z)-OH, t-Boc-Arg (Tos)-OH, t-Boc-Tyr (Br-Z)-OH and t-Boc-Leu-OH, in order. Next, 0.78 g of the carrier resin thus obtained was treated in the same manner as in Example 1 to obtain 253 mg of a crude product. Then, 135 mg of the crude product was purified by HPLC to obtain 57 mg of Compound (I-5).

MS analysis: 1494 (M+1)$^+$

Amino acid analysis: Arg 3.4 (3), Pro 1.1 (1), Tyr 1.9(2), Val 1.1(1), Met 0.4(1), Leu 2.2(2), Lys 1.0(1).

EXAMPLE 5

Synthesis of Compound (I-6: Sequence No. 6)

H-Ser-Leu-Val-Glu-Leu-Val-Ser-Tyr-Tyr-Glu-Lys-His-Ala-OH

In the same manner as in Example 1, 1.7 g of a protected peptide-bound carrier resin was obtained using t-Boc-Ala-bound carrier resin and protected amino acids, t-Boc-His (BOM)-OH, t-Boc-Lys (Cl-Z)-OH, t-Boc-Glu-(OBzl)-OH, t-Boc-Tyr (Br-Z)-OH, t-Boc-Tyr (Br-Z)-OH, t-Boc-Ser (Bzl)-OH, t-Boc-Val-OH, t-Boc-Leu-OH, t-Boc-Glu(OBzl)-OH, t-Boc-Val-OH, t-Boc-Leu-OH and t-Boc-Ser(Bzl)-OH, in order. Next, 0.91 g of the carrier resin thus obtained was treated in the same manner as in Example 1 to obtain 342 mg of a crude product. Then, 70 mg of the crude product was purified by HPLC to obtain 40 mg of Compound (I-6).

MS analysis: 1537 (M+1)$^+$

Amino acid analysis: Glx 2.0 (2), Set 2.1 (2), His 0.9(1), Ala 1.0(1), Tyr 2.0(2), Val 2.0(2), Leu 2.1(2), Lys 1.0 (1).

EXAMPLE 6

Synthesis of Compound (I-7: Sequence No. 7)

H-Tyr-Arg-Lys-Met-Arg-Leu-Arg-Tyr-OH

In the same manner as in Example 1, 1.7 g of a protected peptide-bound carrier resin was obtained using t-Boc-Tyr(Br-Z)-bound carrier resin and protected amino acids, t-Boc-Arg(Tos)-OH, t-Boc-Leu-OH, t-Boc-Arg(Tos)-OH, t-Boc-Met-OH, t-Boc-Lys(Cl-Z)-OH, t-Boc-Arg(Tos)-OH and t-Boc-Tyr(Br-Z)-OH, in order. Next, 0.80 g of the carrier resin thus obtained was treated in the same manner as in Example 1 to obtain 194 mg of a crude product. Then, 67 mg of the crude product was purified by HPLC to obtain 38 mg of Compound (I-7).

MS analysis: 1185 (M+1)$^+$

Amino acid analysis: Arg 3.2 (3), Tyr 1.9 (2), Met 0.9(1), Leu 1.0(1), Lys 1.0(1).

EXAMPLE 7

Synthesis of Compound (I-8: Sequence No. 8)

H-Arg-Lys-Met-Arg-Leu-Arg-OH

In the same manner as in Example 1, 1.5 g of a protected peptide-bound carrier resin was obtained using t-Boc-Arg-(Tos)-bound carrier resin and protected amino acids, t-Boc-Leu-OH, t-Boc-Arg(Tos)-OH, t-Boc-Met-OH, t-Boc-Lys (Cl-Z)-OH and t-Boc-Arg(Tos)-OH in order. Next, 0.80 g of the carrier resin thus obtained was treated in the same manner as in Example 1 to obtain 130 mg of a crude product. Then, 40 mg of the crude product was purified by HPLC to obtain 30 mg of Compound (I-8).

MS analysis: 859 (M+1)$^+$

Amino acid analysis: Arg 3.0(3), Met 0.9(1), Leu 1.0(1), Lys 1.0(1).

EXAMPLE 8

Synthesis of Compound (I-1: Sequence No. 1)

H-Ser-Leu-Val-Glu-Leu-Val-Ser-Tyr-Tyr-Glu-Lys-His-Ala-Leu-Tyr-Arg-Lys-Met-Arg-Leu-Arg-Tyr-Pro-Val-OH

In the same manner as in Example 1, 2.8 g of a protected peptide-bound carrier resin was obtained using t-Boc-Val-bound carrier resin and protected amino acids, t-Boc-Pro-OH, t-Boc-Tyr (Br-Z)-OH, t-Boc-Arg (Tos)-OH, t-Boc-Leu-OH, t-Boc-Arg (Tos)-OH, t-Boc-Met-OH, t-Boc-Lys (Cl-Z)-OH, t-Boc-Arg (Tos)-OH, t-Boc-Tyr (Br-Z)-OH, t-Boc-Leu-OH, t-Boc-Ala-OH, t-Boc-His(DNP)-OH, t-Boc-Lys (Cl-Z)-OH, t-Boc-Glu (OBzl)-OH, t-Boc-Tyr (Br-z)-OH, t-Boc-Tyr (Br-Z)-OH, t-Boc-Ser (Bzl)-OH, t-Boc-Val-OH, t-Boc-Leu-OH, t-Boc-Glu(OBzl)-OH, t-Boc-Val-OH, t-Boc-Leu-OH and t-Boc-Ser(Bzl)-OH in order. Next, 1.3 g of the carrier resin thus obtained was treated in the same manner as in Example 1 to obtain 380 mg of a crude product. Then, 210 mg of the crude product was purified by HPLC to obtain 65 mg of Compound (I-1).

Amino acid analysis: Glx 2.2 (2), Set 1.8 (2), His 1.0(1), Arg 2.6(3), Ala 0.9(1), Pro 1.1(1), Tyr 4.0(4), Val 3.0 (3), Met 1.4 (1), Leu 3.9 (4), Lys 2.0 (2).

EXAMPLE 9

Synthesis of Compound (I-9: Sequence No. 9)

H-Tyr-Arg-Lys-Met-Arg-Leu-Arg-Tyr-NH$_2$

In the same manner as in Example 1, 1.8 g of a protected peptide-bound carrier resin was obtained using 725 mg of p-Methyl-BHA-bound carrier resin and protected amino acids, t-Boc-Tyr(Br-Z)-OH, t-Boc-Arg(Tos)-OH, t-Boc-Leu-OH, t-Boc-Arg(Tos)-OH, t-Boc-Met-OH, t-Boc-Lys(Cl-Z)-OH, t-Boc-Arg (Tos)-OH and t-Boc-Tyr (Br-Z)-OH in order. Next, 0.9 g of the carrier resin thus obtained was treated with hydrogen fluoride in the same manner as in Example 1 to obtain 239.9 mg of a crude product. Then, 140 mg of the crude product was purified by HPLC to obtain 84.8 mg of Compound (I-9).

MS analysis: 1184 $(M+1)^+$

Amino acid analysis: Tyr 2.0 (2), Arg 3.2 (3), Lys 1.1 (1), Met 0.9 (1), Leu 0.9 (1).

EXAMPLE 10

Synthesis of Compound (I-10: Sequence No. 10) $CH_3CO$-Tyr-Arg-Lys-Met -Arg-Leu-Arg-Tyr-$NH_2$ With 725 mg of the carrier resin obtained in Example 9 was condensed 2.0 mmol acetic anhydride to obtain 0.91 g of a carrier resin. The entire amount of the obtained carrier resin was treated with hydrogen fluoride in the same manner as in Example 1 to obtain 217.8 mg of a crude product. Then, 117.8 mg of the crude product was purified by HPLC to obtain 74.5 mg of Compound (I-10).

MS analysis: 1226 $(M+1)^+$

Amino acid analysis: Tyr 2.0(2), Arg 3.2(3), Lys 1.0(1), Met 0.9(1), Leu 0.9(1).

EXAMPLE 11

Synthesis of Compound (I-11: Sequence No. 11)

n-$C_3H_7$CO-Leu-Tyr-Arg-Lys-Met-Arg-Leu-Arg-Tyr-Pro-Val-$NH_2$

In the same manner as in Example 1, 2.1 g of a protected peptide-bound carrier resin was obtained using 725 mg of p-Methyl-BHA-bound carrier resin and protected amino acids, t-Boc-Val-OH, t-Boc-Pro-OH, t-Boc-Tyr(Br-Z)-OH, t-Boc-Arg (Tos)-OH, t-Boc-Leu-OH, t-Boc-Arg (Tos)-OH, t-Boc-Met-OH, t-Boc-Lys(Cl-Z)-OH, t-Boc-Arg(Tos)-OH, t-Boc-Tyr(Br-Z)-OH, t-Boc-Leu-OH and n-butyric anhydride, in order. Next, 0.8 g of the carrier resin thus obtained was treated with hydrogen fluoride in the same manner as in Example 1 to obtain 207 mg of a crude product. Then, 103 mg of the crude product was purified by HPLC to obtain 63 mg of Compound (I-11).

MS analysis: 1563 $(M+1)^+$

Amino acid analysis: Tyr 2.0 (2), Arg 3.0 (3), Lys 1.1(1), Met 1.0(1), Leu 2.0(2), Pro 1.0(1), Val 1.0(1).

EXAMPLE 12

Synthesis Of Compound (I-12: Sequence No. 12)

$C_5H_3O_2$CO-Leu-Tyr-Arg-Lys-Met-Arg-Leu-Arg-Tyr-Pro-Val-$NH_2$

To 60 mg of a 4-(2,4-dimethoxyphenyl-Fmoc-aminomethyl)-phenoxy-bound carrier resin in the reactor of an automatic synthesizer were carried out following treatment and washing procedure according to the synthesis program of Shimadzu Seisakusho.
(1) Washing with DMF (3 minutes)
(2) Treatment with DMF solution containing 30% piperidine (4 minutes×2 times)
(3) Washing with DMF (1 minute×5 times)
(4) To the Val-bonded carrier resin obtained in steps (1)–(3) were added 300 μmol Fmoc-Pro-OH, 300 μmol PyBOP 300 μl HOBt, 450 μl NMM and 10 ml DMF, followed by stirring for 30 minutes.
(5) Washing with DMF (1 minute×5 times)

Thus, Fmoc-Pro-Val was synthesized on the carrier resin. Fmoc-Pro-Val thus obtained was subjected to the above-mentioned washing and deprotecting steps (1)–(3), and Fmoc-Tyr(t-Bu)-OH was added thereto for a condensation reaction in step (4), and Fmoc-Tyr(t-Bu)-Pro-Val was synthesized on the carrier resin after the washing in step (5). Steps (1)–(2) were repeated to obtain a protected peptide-bound carrier resin. In step (4), Fmoc-Arg(Pmc)-OH, Fmoc-Leu-OH, Fmoc-Arg(Pmc)-OH, Fmoc-Met-OH, Fmoc-Lys (t-Boc)-OH, Fmoc-Arg (Pmc)-OH, Fmoc-Tyr (t-Bu)-OH, Fmoc-Leu-OH and coumalic acid were used in order in an amount of 300 μmol. The obtained carrier resin was thoroughly washed with methanol and butyl ether, dried under reduced pressure for 2 hours. To the dried carrier resin in the reactor was added 1 ml 10% TFA/methylene chloride, the mixture was stirred and allowed to drip naturally from the bottom of the reactor, and the liquid was collected. The above-mentioned procedure was repeated 4 times, 1 ml 5% TFA/methylene chloride was added thereto in the same manner, and the above-mentioned procedure was repeated 2 times. The solvent was distilled off from the naturally dripped and collected liquid using an evaporator, and the peptide was cut off from the resin. Further, 1 ml of a solution mixture of 82.5% TFA, 5% $H_2$ 0.5% thioanisol, 2.5% ethanedithiol, 3% ethylmethylsulfide and 2% thiophenol was added thereto, the mixture was allowed to stand at room temperature for 8 hours, and the peptide was deprotected. To the obtained solution was added about 2 ml ether, and 5.7 mg of the resulting precipitate was collected as the crude peptide. The entire amount of the crude product was purified by HPLC using a reverse phase column (NUCLEOSIL 5C18 20×250 mm). The elution was carried out with a linear concentration gradient pattern using acetonitrile containing 0.1% TFA and with detection at 220 nm, fractions containing the desired compound were obtained. The fractions were freeze-dried to obtain 0.52 mg of the captioned compound (I-12).

MS analysis: M+H=1617

Amino acid analysis: Arg 2.9(3), Pro 1.1(1), Tyr 2.0(2), Val 1.1(1), Met 0.9(1), Leu 2.0(2), Lys 1.1(1).

EXAMPLE 13

Synthesis of Compound (I-13: Sequence No. 13)

$(HO)_2C_6H_3$CO-Leu-Tyr-Arg-Lys-Met-Arg-Leu-Arg-Tyr-Pro-Val-$NH_2$

In the same manner as in Example 12, 60 mg of the carrier resin was condensed with the N-protected amino acids, Fmoc-Val-OH, Fmoc-Pro-OH, Fmoc-Tyr(t-Bu)-OH, Fmoc-Arg (Pmc)-OH, Fmoc-Leu-OH, Fmoc-Arg (Pmc)-OH, Fmoc-Met-OH, Fmoc-Lys (t-Boc)-OH, Fmoc-Arg (Pmc)-OH, Fmoc-Tyr (t-Bu)-OH, Fmoc-Leu-OH and 2,3-dihydroxybenzoic acid. The peptide was cleaved from the carrier resin and deprotected in the same manner as in Example 12 to obtain 4.4 mg of a crude product. The entire amount of the crude product was purified by HPLC to obtain 0.49 mg of the desired compound (I-13).

MS analysis: M+H=1631

Amino acid analysis: Arg 2.9(3), Pro 1.1(1), Tyr 2.0 (2), Val 1.1 (1), Met 0.9 (1), Leu 2.0 (2), Lys 1.1 (1).

EXAMPLE 14

Synthesis of Compound (I-14: Sequence No. 14)

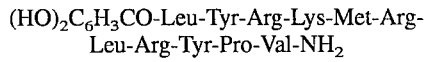
(HO)$_2$C$_6$H$_3$CO-Leu-Tyr-Arg-Lys-Met-Arg-Leu-Arg-Tyr-Pro-Val-NH$_2$ In the same manner as in Example 12, 60 mg of the carrier resin was condensed with the N-protected amino acids, Fmoc-Val-OH, Fmoc-Pro-OH, Fmoc-Tyr(t-Bu)-OH, Fmoc-Arg (Pmc)-OH, Fmoc-Leu-OH, Fmoc-Arg (Pmc)-OH, Fmoc-Met-OH, Fmoc-Lys (t-Boc)-OH, Fmoc-Arg (Pmc)-OH, Fmoc-Tyr (t-Bu)-OH, Fmoc-Leu-OH and 2,4-dihydroxybenzoic acid. The peptide was cleaved from the carrier resin and deprotected in the same manner as in Example 12 to obtain 5.0 mg of a crude product. The entire amount of the crude product was purified by HPLC to obtain 1.05 mg of the desired compound (I-14).

MS analysis: M+H=1631

Amino acid analysis: Arg 3.1 (3), Pro 1.0 (1), Tyr 2.0(2), Val 1.0(1), Met 0.8(1), Leu 2.0(2), Lys 1.0(1).

EXAMPLE 15

Synthesis of Compound (I-15: Sequence No. 15)

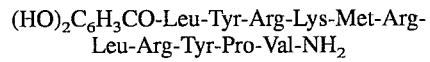
(HO)$_2$C$_6$H$_3$CO-Leu-Tyr-Arg-Lys-Met-Arg-Leu-Arg-Tyr-Pro-Val-NH$_2$ In the same manner as in Example 12, 60 mg of the carrier resin was condensed with the N-protected amino acids, Fmoc-Val-OH, Fmoc-Pro-OH, Fmoc-Tyr(t-Bu)-OH, Fmoc-Arg (Pmc)-OH, Fmoc-Leu-OH, Fmoc-Arg (Pmc)-OH, Fmoc-Met-OH, Fmoc-Lys (t-Boc)-OH, Fmoc-Arg (Pmc)-OH, Fmoc-Tyr (t-Bu)-OH, Fmoc-Leu-OH and 2,5-dihydroxybenzoic acid. The peptide was cleaved from the carrier resin and deprotected in the same manner as in Example 12 to obtain 6.0 mg of a crude product. The entire amount of the crude product was purified by HPLC to obtain 1.27 mg of the desired compound (I-15).

MS analysis: M+H=1631

Amino acid analysis: Arg 3.0(3), Pro 1.0(1), Tyr 2.0(2), Val 1.0(1), Met 0.9(1), Leu 2.0(2), Lys 1.0(1).

EXAMPLE 16

Synthesis of Compound (I-16: Sequence No. 16)

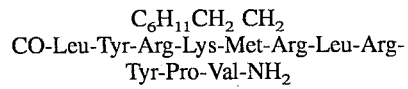
C$_6$H$_{11}$CH$_2$ CH$_2$CO-Leu-Tyr-Arg-Lys-Met-Arg-Leu-Arg-Tyr-Pro-Val-NH$_2$ In the same manner as in Example 12, 60 mg of the carrier resin was condensed with the N-protected amino acids, Fmoc-Val-OH, Fmoc-Pro-OH, Fmoc-Tyr(t-Bu)-OH, Fmoc-Arg (Pmc)-OH, Fmoc-Leu-OH, Fmoc-Arg (Pmc)-OH, Fmoc-Met-OH, Fmoc-Lys (t-Boc)-OH, Fmoc-Arg (Pmc)-OH, Fmoc-Tyr(t-Bu)-OH, Fmoc-Leu-OH and 3-cyclohexanepropionic acid. The peptide was cleaved from the carrier resin and deprotected in the same manner as in Example 12 to obtain 3.4 mg of a crude product. The entire amount of the crude product was purified by HPLC to obtain 1.25 mg of the desired compound (I-16).

MS analysis: M+H=1633

Amino acid analysis: Arg 3.0(3), Pro 1.0(1), Tyr 2.0(2), Val 1.0(1), Met 0.9(1), Leu 2.0(2), Lys 1.1(1).

EXAMPLE 17

Synthesis of Compound (I-17: Sequence No. 17)

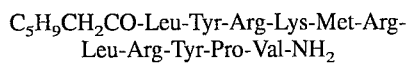
C$_5$H$_9$CH$_2$CO-Leu-Tyr-Arg-Lys-Met-Arg-Leu-Arg-Tyr-Pro-Val-NH$_2$

In the same manner as in Example 12, 60 mg of the carrier resin was condensed with the N-protected amino acids, Fmoc-Val-OH, Fmoc-Pro-OH, Fmoc-Tyr(t-Bu)-OH, Fmoc-Arg (Pmc)-OH, Fmoc-Leu-OH, Fmoc-Arg (Pmc)-OH, Fmoc-Met-OH, Fmoc-Lys (t-Boc)-OH, Fmoc-Arg (Pmc)-OH, Fmoc-Tyr(t-Bu)-OH, Fmoc-Leu-OH and cyclopentylacetic acid. The peptide was cleaved from the carrier resin and deprotected in the same manner as in Example 12 to obtain 3.7 mg of a crude product. The entire amount of the crude product was purified by HPLC to obtain 1.0 mg of the desired compound (I-17).

MS analysis: M+H=1605

Amino acid analysis: Arg 3.0(3), Pro 1.0(1), Tyr 2.1(2), Val 1.0(1), Met 0.9(1), Leu 2.0(2), Lys 1.0(1).

EXAMPLE 18

Synthesis of Compound (I-18: Sequence No. 18)

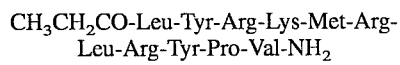
CH$_3$CH$_2$CO-Leu-Tyr-Arg-Lys-Met-Arg-Leu-Arg-Tyr-Pro-Val-NH$_2$

In the same manner as in Example 12, 60 mg of the carrier resin was condensed with the N-protected amino acids, Fmoc-Val-OH, Fmoc-Pro-OH, Fmoc-Tyr(t-Bu)-OH, Fmoc-Arg (Pmc)-OH, Fmoc-Leu-OH, Fmoc-Arg (Pmc)-OH, Fmoc-Met-OH, Fmoc-Lys (t-Boc)-OH, Fmoc-Arg (Pmc)-OH, Fmoc-Tyr(t-Bu)-OH, Fmoc-Leu-OH and propionic acid. The peptide was cleaved from the carrier resin and deprotected in the same manner as in Example 12 to obtain 24.5 mg of a crude product. Then, 14.8 mg of the crude product was purified by HPLC to obtain 6.0 mg of the desired compound (I-18).

MS analysis: M+H=1551

Amino acid analysis: Arg 3.0 (3), Pro 0.9 (1), Tyr 2.0(2), Val 1.0(1), Met 0.9(1), Leu 2.0(2), Lys 1.0(1).

EXAMPLE 19

Synthesis of Compound (I-19: Sequence No. 19)

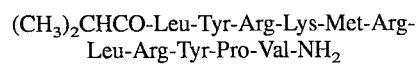
(CH$_3$)$_2$CHCO-Leu-Tyr-Arg-Lys-Met-Arg-Leu-Arg-Tyr-Pro-Val-NH$_2$

In the same manner as in Example 12, 60 mg of the carrier resin was condensed with the N-protected amino acids, Fmoc-Val-OH, Fmoc-Pro-OH, Fmoc-Tyr(t-Bu)-OH, Fmoc-Arg (Pmc)-OH, Fmoc-Leu-OH, Fmoc-Arg (Pmc)-OH, Fmoc-Met-OH, Fmoc-Lys (t-Boc)-OH, Fmoc-Arg (Pmc)-OH, Fmoc-Tyr(t-Bu)-OH, Fmoc-Leu-OH and isobutyric acid. The peptide was cleaved from the carrier resin and deprotected in the same manner as in Example 12 to obtain 24.9 mg of a crude product. Then, 14.8 mg of the crude product was purified by HPLC to obtain 6.2 mg of the desired compound (I-19).

MS analysis: M+H=1565

Amino acid analysis: Arg 3.1(3), Pro 1.0(1), Tyr 2.0(2), Val 1.0(1), Met 0.9(1), Leu 2.0(2), Lys 1.0(1).

EXAMPLE 20

Synthesis of Compound (I-20: Sequence No. 20)

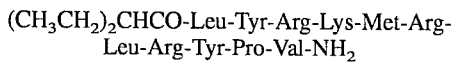

In the same manner as in Example 12, 60 mg of the carrier resin was condensed with the N-protected amino acids, Fmoc-Val-OH, Fmoc-Pro-OH, Fmoc-Tyr(t-Bu)-OH, Fmoc-Arg (Pmc)-OH, Fmoc-Leu-OH, Fmoc-Arg (Pmc)-OH, Fmoc-Met-OH, Fmoc-Lys(t-Boc)-OH, Fmoc-Arg(Pmc)-OH, Fmoc-Tyr(t-Bu)-OH, Fmoc-Leu-OH and 2-ethyl-n-butyric acid. The peptide was cleaved from the carrier resin and deprotected in the same manner as in Example 12 to obtain 30.6 mg of a crude product. Then, 16.8 mg of the crude product was purified by HPLC to obtain 7.1 mg of the desired compound (I-20).

MS analysis: M+H=1593

Amino acid analysis: Arg 3.0(3), Pro 1.0(1), Tyr 2.1(2), Val 1.1(1), Met 0.9(1), Leu 2.0(2), Lys 1.0(1).

EXAMPLE 21

Synthesis of Compound (I-21: Sequence No. 21)

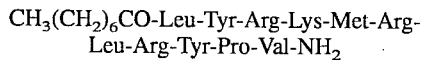

In the same manner as in Example 12, 60 mg of the carrier resin was condensed with the N-protected amino acids, Fmoc-Val-OH, Fmoc-Pro-OH, Fmoc-Tyr(t-Bu)-OH, Fmoc-Arg (Pmc)-OH, Fmoc-Leu-OH, Fmoc-Arg (Pmc)-OH, Fmoc-Met-OH, Fmoc-Lys (t-Boc)-OH, Fmoc-Arg (Pmc)-OH, Fmoc-Tyr(t-Bu)-OH, Fmoc-Leu-OH and n-caprylic acid. The peptide was cleaved from the carrier resin and deprotected in the same manner as in Example 12 to obtain 23.9 mg of a crude product. Then, 14.2 mg of the crude product was purified by HPLC to obtain 4.7 mg of the desired compound (I-21).

MS analysis: M+H=1621

Amino acid analysis: Arg 3.1 (3), Pro 1.0 (1), Tyr 2.1(2), Val 1.0(1), Met 0.9(1), Leu 2.0(2), Lys 1.0(1).

EXAMPLE 22

Synthesis of Compound (I-22: Sequence No. 22)

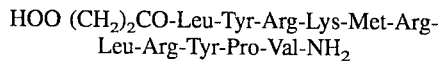

In the same manner as in Example 12, 60 mg of the carrier resin was condensed with the N-protected amino acids, Fmoc-Val-OH, Fmoc-Pro-OH, Fmoc-Tyr(t-Bu)-OH, Fmoc-Arg (Pmc)-OH, Fmoc-Leu-OH, Fmoc-Arg (Pmc)-OH, Fmoc-Met-OH, Fmoc-Lys (t-Boc)-OH, Fmoc-Arg (Pmc)-OH, Fmoc-Tyr(t-Bu)-OH, Fmoc-Leu-OH and succinic anhydride. The peptide was cleaved from the carrier resin and deprotected in the same manner as in Example 12 to obtain 29.6 mg of a crude product. Then, 17.4 mg of the crude product was purified by HPLC to obtain 7.0 mg of the desired compound (I-22).

MS analysis: M+H=1595

Amino acid analysis: Arg 3.1(3), Pro 1.0(1), Tyr 2.1 (2), Val 1.0 (1), Met 0.9 (1), Leu 2.0 (2), Lys 1.0 (1).

EXAMPLE 23

Compound (I-23: Sequence No. 23)

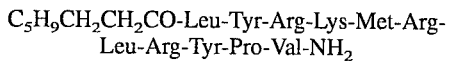

In the same manner as in Example 12, 60 mg of the carrier resin was condensed with the N-protected amino acids, Fmoc-Val-OH, Fmoc-Pro-OH, Fmoc-Tyr(t-Bu)-OH, Fmoc-Arg (Pmc)-OH, Fmoc-Leu-OH, Fmoc-Arg (Pmc)-OH, Fmoc-Met-OH, Fmoc-Lys (t-Boc)-OH, Fmoc-Arg (Pmc)-OH, Fmoc-Tyr(t-Bu)-OH, Fmoc-Leu-OH and 3-cyclopentylpropionic acid. The peptide was cleaved from the carrier resin and deprotected in the same manner as in Example 12 to obtain 3.7 mg of a crude product. The entire amount of the crude product was purified by HPLC to obtain 0.29 mg of the desired compound (I-23).

MS analysis: M+H=1619

Amino acid analysis: Arg 3.2(3), Pro 1.0(1), Tyr 2.0 (2), Val 1.1 (1), Met 0.9 (1), Leu 1.9 (2), Lys 1.0 (1).

EXAMPLE 24

Compound (I-24: Sequence No. 24)

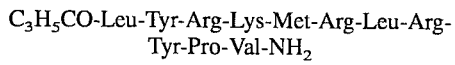

In the same manner as in Example 12, 60 mg of the carrier resin was condensed with the N-protected amino acids, Fmoc-Val-OH, Fmoc-Pro-OH, Fmoc-Tyr(t-Bu)-OH, Fmoc-Arg (Pmc)-OH, Fmoc-Leu-OH, Fmoc-Arg (Pmc)-OH, Fmoc-Met-OH, Fmoc-Lys (t-Boc)-OH, Fmoc-Arg (Pmc)-OH, Fmoc-Tyr(t-Bu)-OH, Fmoc-Leu-OH and cyclopropanecarboxylic acid. The peptide was cleaved from the carrier resin and deprotected in the same manner as in Example 12 to obtain 5.6 mg of a crude product. Then, 3.0 mg of the crude product was purified by HPLC to obtain 0.88 mg of the desired compound (I-24).

MS analysis: M+H=1563

Amino acid analysis: Arg 3.1(3), Pro 1.0(1), Tyr 2.0(2), Val 1.0(1), Met 0.9(1), Leu 1.9(2), Lys 1.0(1).

EXAMPLE 25:

Compound (I-25: Sequence No. 25)

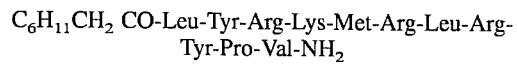

In the same manner as in Example 12, 60 mg of the carrier resin was condensed with the N-protected amino acids, Fmoc-Val-OH, Fmoc-Pro-OH, Fmoc-Tyr(t-Bu)-OH, Fmoc-Arg (Pmc)-OH, Fmoc-Leu-OH, Fmoc-Arg (Pmc)-OH, Fmoc-Met-OH, Fmoc-Lys (t-Boc)-OH, Fmoc-Arg (Pmc)-OH, Fmoc-Tyr(t-Bu)-OH, Fmoc-Leu-OH and cyclohexylacetic acid. The peptide was cleaved from the carrier resin and deprotected in the same manner as in Example 12 to obtain 11.4 mg of a crude product. Then, 5.9 mg of the crude product was purified by HPLC to obtain 3.91 mg of the desired compound (I-25).

MS analysis: M+H=1619

Amino acid analysis: Arg 3.1(3), Pro 1.0(1), Tyr 2.0(2), Val 1.0(1), Met 1o0(1), Leu 1.9(2), Lys 1.0(1).

EXAMPLE 26

Compound (I-26: Sequence No. 26)

$$C_5H_9CO\text{-Leu-Tyr-Arg-Lys-Met-Arg-Leu-Arg-Tyr-pro-Val-}NH_2$$

In the same manner as in Example 12, 60 mg of the carrier resin was condensed with the N-protected amino acids, Fmoc-Val-OH, Fmoc-Pro-OH, Fmoc-Tyr(t-Bu)-OH, Fmoc-Arg (Pmc)-OH, Fmoc-Leu-OH, Fmoc-Arg (Pmc)-OH, Fmoc-Met-OH, Fmoc-Lys (t-Boc)-OH, Fmoc-Arg (Pmc)-OH, Fmoc-Tyr(t-Bu)-OH, Fmoc-Leu-OH and cyclopentanecarboxylic acid. The peptide was cleaved from the carrier resin and deprotected in the same manner as in Example 12 to obtain 13.0 mg of a crude product. Then, 6.5 mg of the crude product was purified by HPLC to obtain 3.75 mg of the desired compound (I-26).

MS analysis: M+H=1591

Amino acid analysis: Arg 3.0(3), Pro 1.0(1), Tyr 2.0(2), Val 1.0(1), Met 1.0(1), Leu 2.0(2), Lys 1.0(1).

EXAMPLE 27

Compound (I-27: Sequence No.. 27).

$$CH_3(CH_2)_4CO\text{-Leu-Tyr-Arg-Lys-Met-Arg-Leu-Arg-Tyr-Pro-Val-}NH_2$$

In the same manner as in Example 12, 60 mg of the carrier resin was condensed with the N-protected amino acids, Fmoc-Val-OH, Fmoc-Pro-OH, Fmoc-Tyr(t-Bu)-OH, Fmoc-Arg (Pmc)-OH, Fmoc-Leu-OH, Fmoc-Arg (Pmc)-OH, Fmoc-Met-OH, Fmoc-Lys(t-Boc)-OH, Fmoc-Arg(Pmc)-OH, Fmoc-Tyr(t-Bu)-OH, Fmoc-Leu-OH and n-caproic acid. The peptide was cleaved from the carrier resin and deprotected in the same manner as in Example 12 to obtain 12.7 mg of a crude product. Then, 6.5 mg of the crude product was purified by HPLC to obtain 3.63 mg of the desired compound (I-27).

MS analysis: M+H=1593

Amino acid analysis: Arg 3.0(3), Pro 1.0(1), Tyr 2.0(2), Val 1.0(1), Met 1.1(1), Leu 2.0(2), Lys 1.0(1).

EXAMPLE 28

Compound (I-28: Sequence No. 28)

$$CH_3(CH_2)_7CO\text{-Leu-Tyr-Arg-Lys-Met-Arg-Leu-Arg-Tyr-Pro-Val-}NH_2$$

In the same manner as in Example 12, 60 mg of the carrier resin was condensed with the N-protected amino acids, Fmoc-Val-OH, Fmoc-Pro-OH, Fmoc-Tyr(t-Bu)-OH, Fmoc-Arg (Pmc)-OH, Fmoc-Leu-OH, Fmoc-Arg (Pmc)-OH, Fmoc-Met-OH, Fmoc-Lys (t-Boc)-OH, Fmoc-Arg (Pmc)-OH, Fmoc-Tyr(t-Bu)-OH, Fmoc-Leu-OH and pelargonic acid. The peptide was cleaved from the carrier resin and deprotected in the same manner as in Example 12 to obtain 10.6 mg of a crude product. Then, 5.4 mg of the crude product was purified by HPLC to obtain 2.45 mg of the desired compound (I-28).

MS analysis: M+H=1635

Amino acid analysis: Arg 2.9 (3), Pro 1.1 (1), Tyr 2.0(2), Val 1.0(1), Met 1.0(1), Leu 2.0(2), Lys 1.0(1).

INDUSTRIAL APPLICABILITY

According to the present invention, Compound (I) having PLC-inhibiting activity may be provided.

---

We claim:

1. A peptide which has phospholipase C-inhibiting activity and which is selected from the peptides having the amino acid sequences defined in Sequence Listing SEQ. ID: Nos. 1–8.

2. A peptide which has the following amino acid sequence:

W-X-Tyr-Arg-Lys-Met-Arg-Leu-Arg-Tyr-Y-Z where W represents a hydrogen atom, a substituted or unsubstituted alkanoyl group, a substituted unsubstituted aroyl group or a coumalil group; X represents a single bond or -Leu-; Y represents a single bond or -Pro-Val-; and Z represents an amino group when W represents a hydrogen atom.

3. The peptide according to claim 2, which is selected from the peptides having the amino acid sequences defined in Sequence Listing by SEQ ID: Nos. 9–28.

* * * * *